US008679116B2

(12) United States Patent
Cheng et al.

(10) Patent No.: US 8,679,116 B2
(45) Date of Patent: Mar. 25, 2014

(54) MULTIPLE AXES EXTERNAL BONE FIXING MEMBER (75) Inventors: Cheng-Kung Cheng, Taipei (TW); Chan-Tsung Yang, Taipei (TW); Yu-Shu Lai, Taipei (TW); Jou-Wen Chen, New Taipei (TW)

(73) Assignee: National Yang-Ming University, Taipei (TW)

( * ) Notice: Subject to any disclaimer, the term of this patent is extended or adjusted under 35 U.S.C. 154(b) by 0 days.

(21) Appl. No.: 13/490,902

(22) Filed: Jun. 7, 2012

(65) Prior Publication Data
US 2013/0253511 A1 Sep. 26, 2013

(30) Foreign Application Priority Data

Mar. 22, 2012 (TW) .............................. 101205176 U (51) Int. Cl.
*A61B 17/64* (2006.01)
(52) U.S. Cl.
USPC ............................................ 606/54; 606/287
(58) Field of Classification Search
USPC ...................... 606/70, 71, 280–299
See application file for complete search history.

(56) References Cited

U.S. PATENT DOCUMENTS

| 5,201,733 | A | | 4/1993 | Etheredge, III | |
|---|---|---|---|---|---|
| 5,591,166 | A | * | 1/1997 | Bernhardt et al. | 606/266 |
| 5,607,428 | A | * | 3/1997 | Lin | 606/287 |
| 5,800,435 | A | * | 9/1998 | Errico et al. | 606/261 |
| 6,287,309 | B1 | * | 9/2001 | Baccelli et al. | 606/292 |
| 6,315,779 | B1 | * | 11/2001 | Morrison et al. | 606/281 |
| 6,547,790 | B2 | * | 4/2003 | Harkey et al. | 606/250 |
| 7,794,477 | B2 | * | 9/2010 | Melkent et al. | 606/246 |
| 7,883,531 | B2 | * | 2/2011 | de Coninck | 606/290 |
| 8,262,657 | B2 | * | 9/2012 | Hajianpour | 606/59 |
| 2003/0105462 | A1 | | 6/2003 | Haider | |
| 2004/0006342 | A1 | * | 1/2004 | Altarac et al. | 606/61 |
| 2004/0260223 | A1 | | 12/2004 | Roukis et al. | |
| 2005/0043730 | A1 | | 2/2005 | Janowski | |
| 2005/0234456 | A1 | * | 10/2005 | Malandain | 606/69 |
| 2005/0277923 | A1 | * | 12/2005 | Sweeney | 606/61 |
| 2007/0055234 | A1 | | 3/2007 | McGrath et al. | |
| 2007/0161984 | A1 | | 7/2007 | Cresina et al. | |
| 2009/0093849 | A1 | | 4/2009 | Grabowski | |
| 2009/0216282 | A1 | | 8/2009 | Blake et al. | |
| 2009/0287215 | A1 | * | 11/2009 | Fisher et al. | 606/71 |
| 2009/0326532 | A1 | | 12/2009 | Schulze | |
| 2011/0071573 | A1 | * | 3/2011 | Sixto et al. | 606/286 |
| 2011/0190770 | A1 | | 8/2011 | Suh | |
| 2012/0150239 | A1 | * | 6/2012 | Garamszegi | 606/328 |

* cited by examiner

*Primary Examiner* — Jerry Cumberledge
(74) *Attorney, Agent, or Firm* — Muncy, Geissler, Olds & Lowe, P.C.

(57) ABSTRACT

An external bone fixing member includes an external reconstruction plate to replace the conventional large external support frame to reduce the volume of the external fixing member and the external bone fixing member is cooperated with a screw which is angle adjustable so as to meet requirements of fixation of the fractured bones (limb bones) at different positions or comminuted fractures. The use of the screw is further cooperated with the reconstruction plate to reinforce the stability of the connection between the reconstruction plate and the screw to prevent the screw from withdrawing, moving, angle changing or movement of the reconstruction plate.

5 Claims, 10 Drawing Sheets

MULTIPLE AXES EXTERNAL BONE FIXING MEMBER

FIELD OF THE INVENTION

The present invention relates to fixation of bone fracture, and more particularly, to an external fixing member having at least one screw connected with a reconstruction plate to achieve the purposes of fixation and anatomical configuration of the bone fracture. The present invention is especially suitable for comminuted fracture and the fractured bones of four limbs.

BACKGROUND OF THE INVENTION

The fixations for bone fractures generally comprise internal fixation and external fixation according to the areas and complexity of the fractures.

The internal fixation of fractures utilizes metallic screws, reconstruction plates, bone marrow screws to directly fix the fractured bones from inside or outside thereof. The major benefit of the internal fixation is to provide strong support or compressing feature to the fractured area to keep the fractured bones in correct anatomical configuration and maintain the stable circumstance during the period of restoration of the fractured area. There is no object projecting from the body and the limitation to the patient is reduced. The related disclosures of prior art are disclosed in U.S. Pat. No. 5,201,733, US20030105462 and US20090093849.

Figure 1:
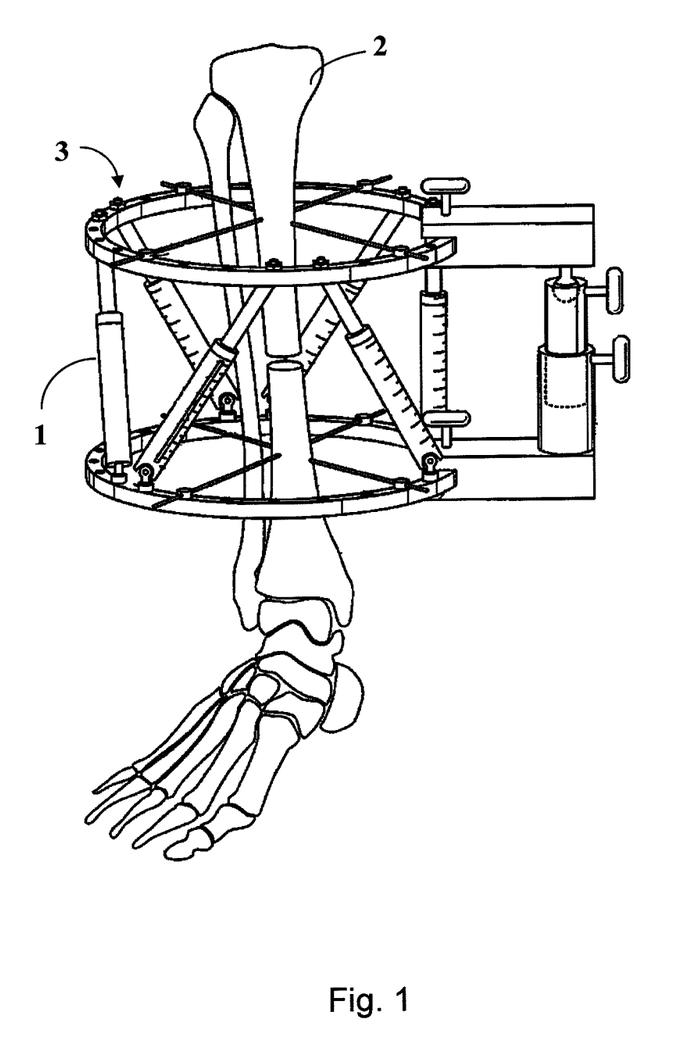
FIG. 1. shows the external fixation of the prior art.

The external fixation of fractures utilizes multiple bars 1 which are located in the patient's body and connected with the fractured bones 2, as shown in FIG. 1. The bars 1 are connected with a connector located externally to the patient's body to form a support frame 3. The support frame 3 is installed to the outside of the area of fractured bones 2 to provide the support among a larger area. This way provides firm support to the open fracture or comminuted fracture. The related disclosures of prior art are disclosed in US Patent No. US20090216282, US20110190770, US20040260223, US20050043730, US20090326532, US20070055234 and US20070161984. The drawback of the external connector is that the support frame 3 is too bulky which is not convenient for the everyday living and the scope of the activities of the patients.

SUMMARY OF THE INVENTION

The present invention intends to provide a new external bone fixing member which uses the external reconstruction plate to replace the bulky external support frame and the volume of the external bone fixing member is reduced. The present invention further provides a screw wherein the angular positions of the screw can be adjusted to meet requirements of fixation of the fractured bones (limb bones) at different positions or comminuted fractures. The use of the screw is further cooperated with the reconstruction plate to reinforce the stability of the connection between the reconstruction plate and the screw to prevent the screw from withdrawing, moving, angle changing or movement of the reconstruction plate.

The external bone fixing member of the present invention is named multiple axes external reconstruction plate bone fixing member which provides strong support to the fractured area to complete the fixation and anatomical configuration of the bone fracture, the debridement space is also preserved. Compared with the conventional external fixing member, the inconvenience of activities of the patient after surgery is reduced and provides more operational benefits to the clinical surgeries.

In order to achieve the above mentioned objects, the external bone fixing member of the present invention comprises an external reconstruction plate which comprises multiple locking portions and a connection member is connected to the locking portion. A screw extends through the connection member and the external reconstruction plate. The head of the screw is a convex and curved head which is rotatably cooperated with the concaved and curved inner wall of the connection member to allow the screw to change to different angles. The connection member has a locking member and a pressing plate to secure the screw to prevent the screw from withdrawing and moving.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 2:
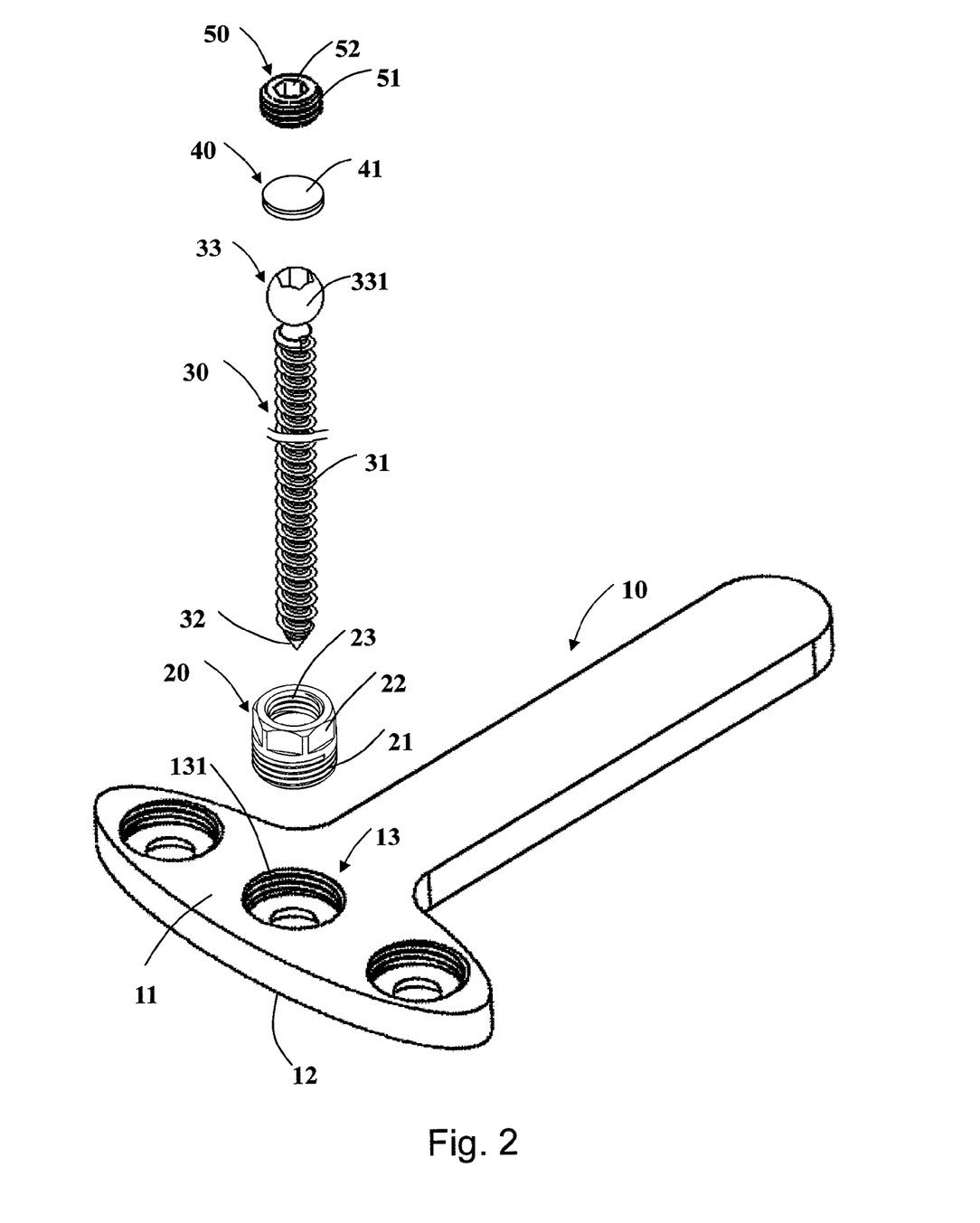
FIG. 2 is an exploded view to show the external bone fixing member of the present invention.

Referring to FIG. 2, the external bone fixing member of the present invention comprises an external reconstruction plate 10, at least one connection member 20, at least one screw 30, at least one pressing plate 40 and at least one locking member 50.

Figure 4:
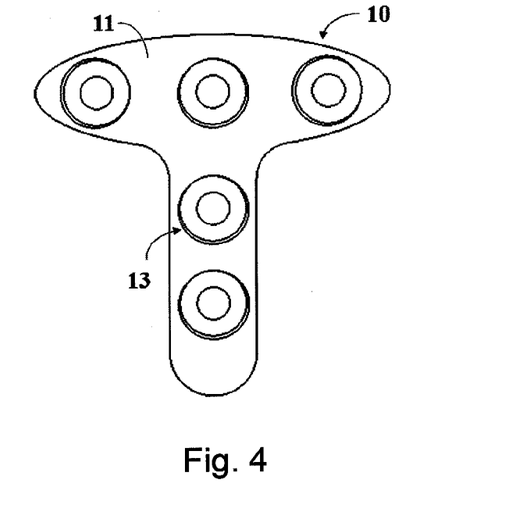
FIG. 4 shows the cross sectional view of the external reconstruction plate of another preferred embodiment of the present invention.

FIG. 4 shows the external reconstruction plate 10, however, the external reconstruction plate 10 of the present invention is not restricted as disclosed, the outer appearance, the length, the width and the thickness can be designed as any geometric shape according the applied areas. The external reconstruction plate 10 has multiple locking portions 13 and each locking portion 13 has an inner threaded hole 131 and a through hole 132. The inner threaded hole 131 extends into the external reconstruction plate 10 a depth from the top surface of the external reconstruction plate 10, and the through hole 132 extends into the external reconstruction plate 10 a depth from the bottom surface of the external reconstruction plate 10. The through hole 132 is a cone-shaped hole with a small opening which communicates with the inner threaded hole 131 and shares the common axis of the inner threaded hole 131. The locking portions 13 can be allocated at different positions depending on the shape and function of the external reconstruction plate 10. The disclosed positions are not restricted for the invention.

Figure 3:
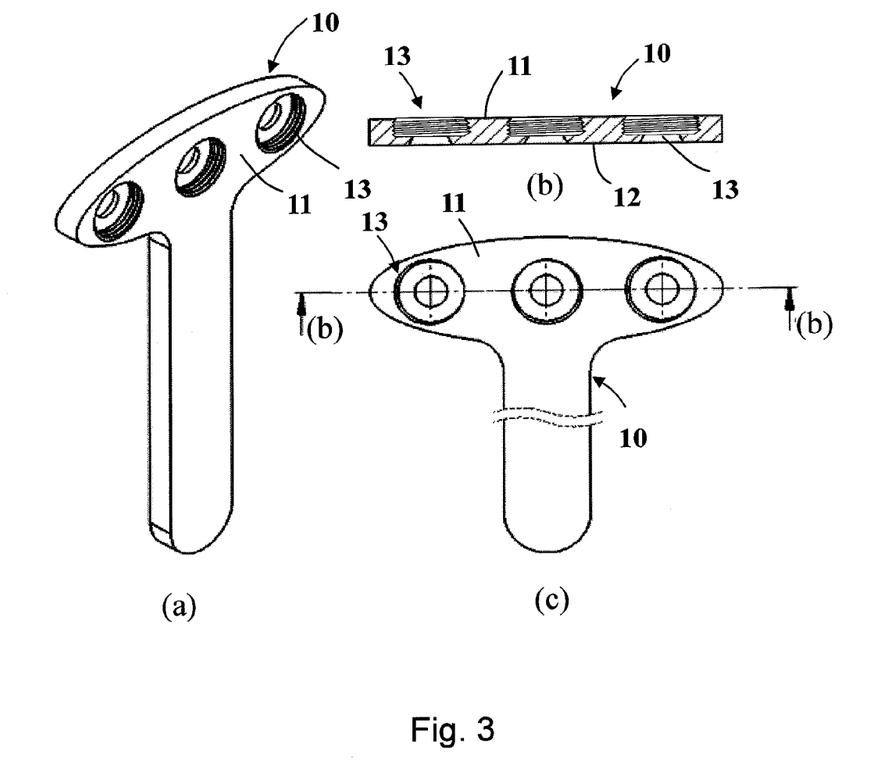
FIG. 3 shows the perspective view (a), the plan view (b) and the cross sectional view (c) of the external reconstruction plate of one preferred embodiment of the present invention.

FIG. 4 shows the cross sectional view of the external reconstruction plate of another preferred embodiment of the present invention. The only difference between the FIG. 3 and FIG. 4 is that the number and location of the locking portions 13 of the external reconstruction plate 10.

Figure 5:
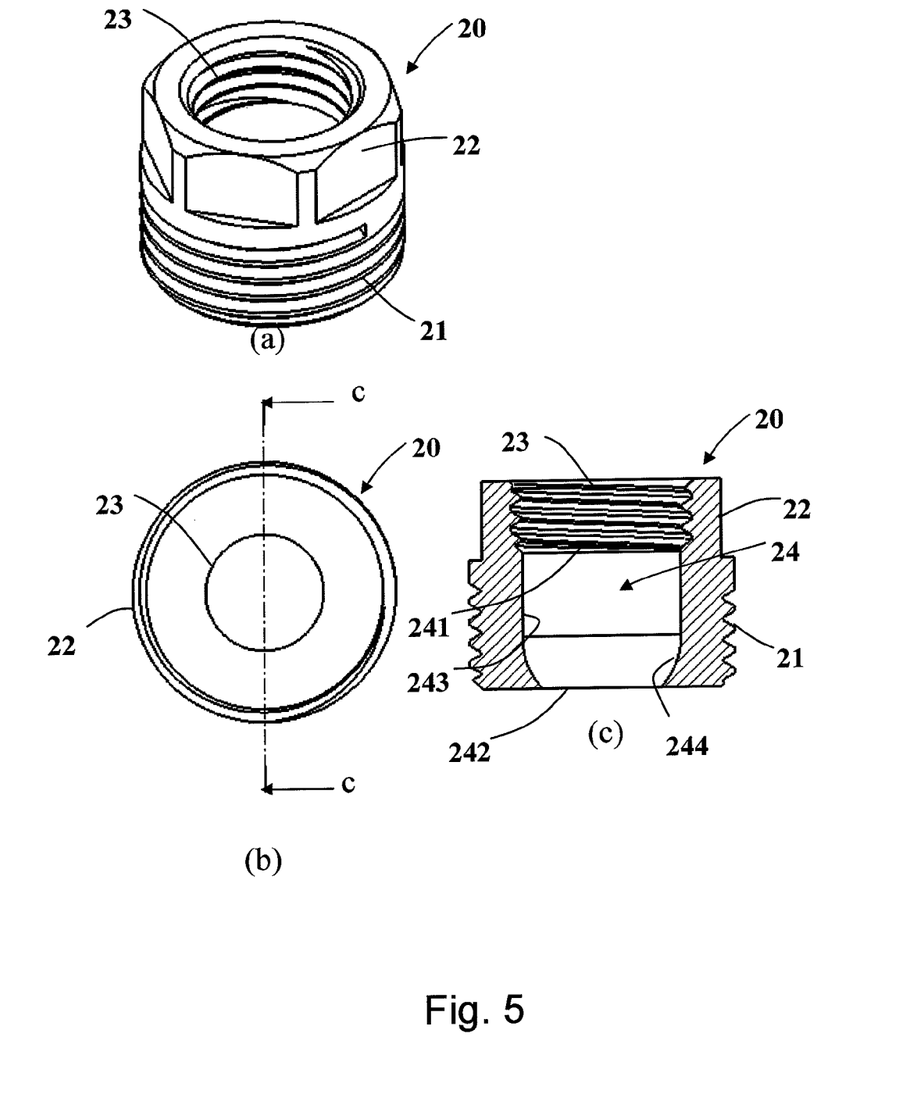
FIG. 5 shows the perspective view (a), the end view (b) and the cross sectional view (c) of the connection member of the present invention.
Figure 9:
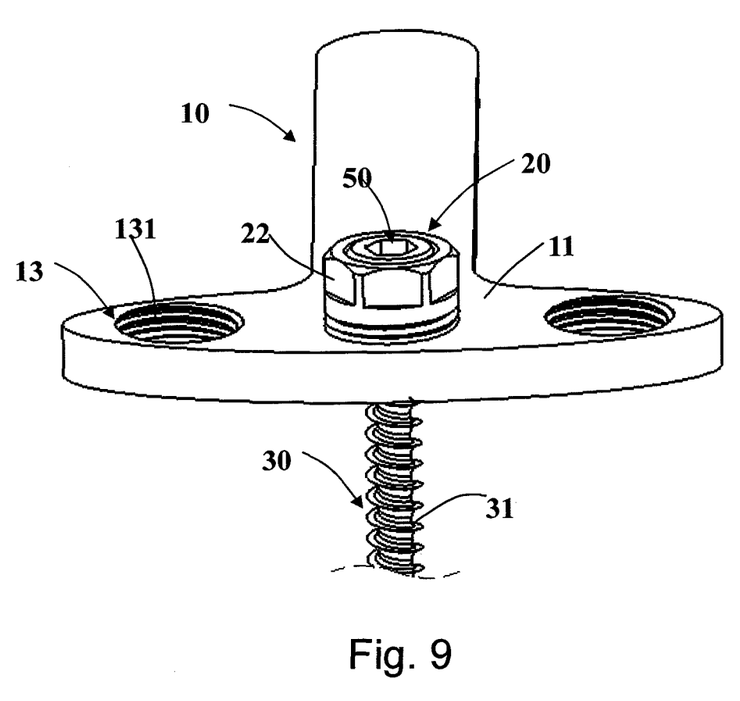
FIG. 9 is a perspective view to show the external bone fixing member of the present invention.
Figure 10:
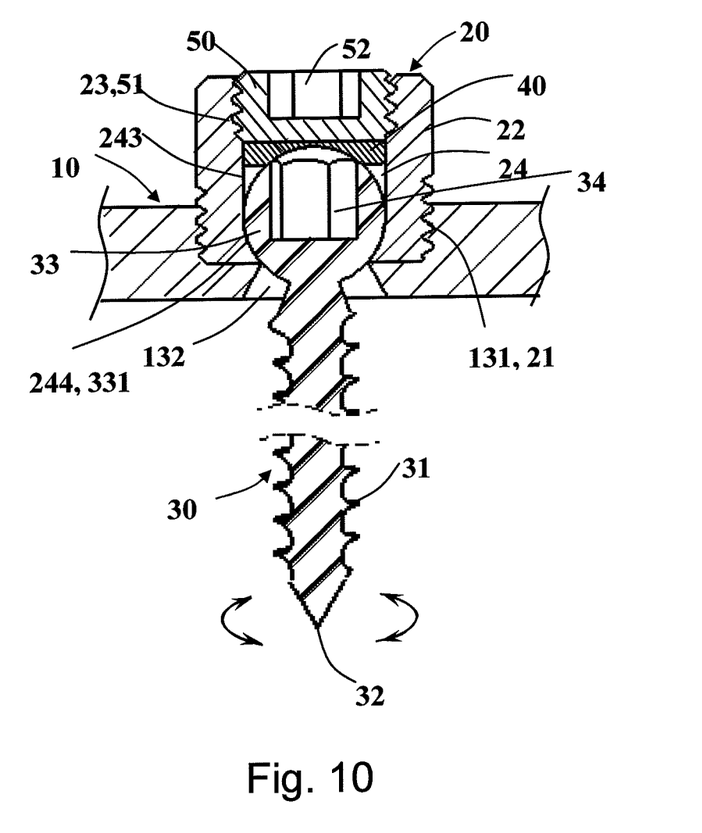
FIG. 10 is a cross sectional view of the external bone fixing member of the present invention.

As shown in FIGS. 5, 9 and 10, the connection member 20 and the connection with other parts are disclosed, wherein the connection member 20 is a ring-shaped member and has an outer threaded section 21 and a polygonal section 22. The connection member 20 has an inner threaded hole 23 and a reception hole 24 which communicates with the inner threaded hole 23 of the connection member 20. The top end diameter 241 of the reception hole 24 of the connection member 20 is larger than the bottom end diameter 242 of the reception hole 24 of the connection member 20. The inner wall 243 that is located adjacent to the top end diameter 241 is a vertical wall. The reception hole 24 has a concaved and curved inner wall 244 which is located adjacent to the bottom end diameter 242. The connection member 20 can be rotated by using a tool (not shown) to operate the polygonal section 22. The outer threaded section 21 is threadedly connected with the inner threaded hole 13 of the locking portion 13 of the external reconstruction plate 10.

Figure 6:
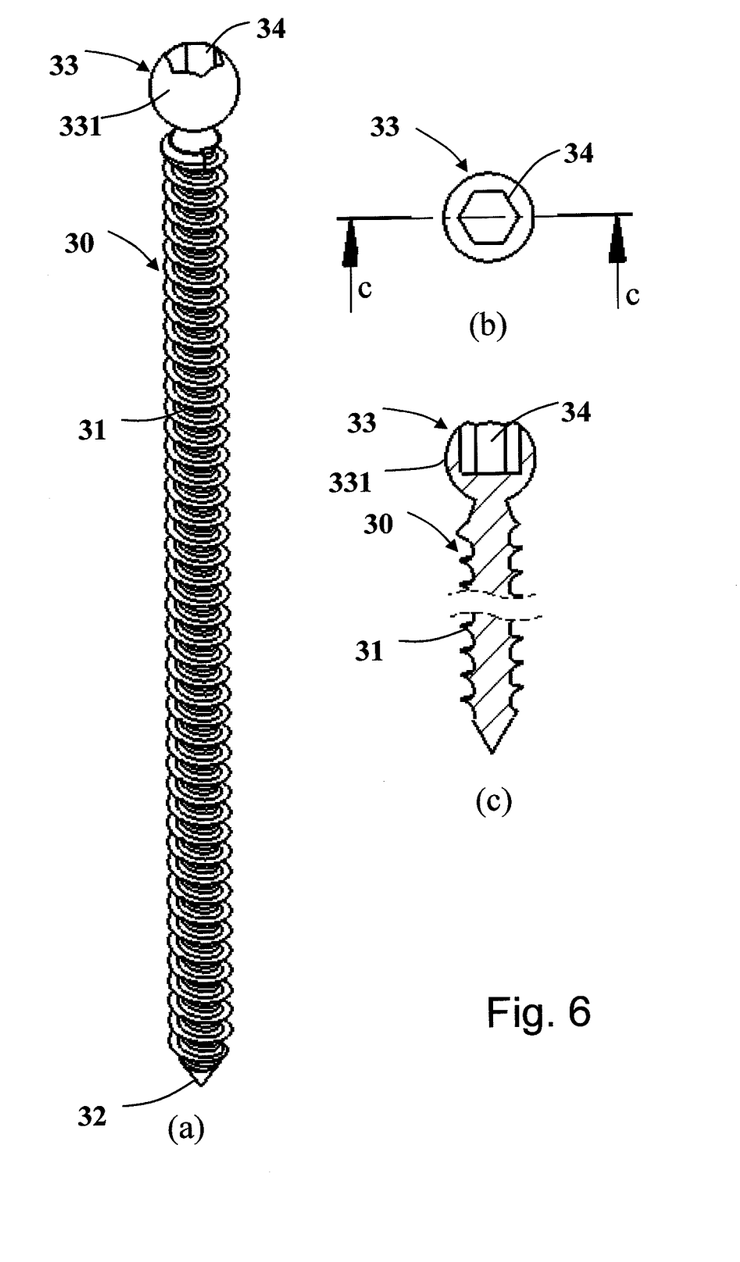
FIG. 6 shows the perspective view (a), the end view (b) and the cross sectional view (c) of the screw of the present invention.

FIGS. 6, 9 and 10 disclose the screw 30 which has a shank 31 with outer threads. The lower end of the shank 31 is a self tapping end 32 which is a tip end in this embodiment, and a head 33 is connected to the top end of the shank 31. The head 33 has a convex and curved outer wall 331 and a first recess 34 is defined in the top of the head 33 so as to be cooperated with a tool (not shown). The screw 30 extends through the connection member 20 and the external reconstruction plate 10, and the self tapping end 32 and the shank with the outer threads is locked to the bone. The head 33 of the screw 30 is accommodated in the reception hole 24 of the connection member 20. The concaved and curved inner wall 244 is matched with the convex and curved outer wall 331, and the cone-shaped through hole 132 of the external reconstruction plate 10 provides the space for the screw 10, so that the screw 10 is pivotable and can be set at different directions to fix and align the fractured bones.

Figure 7:
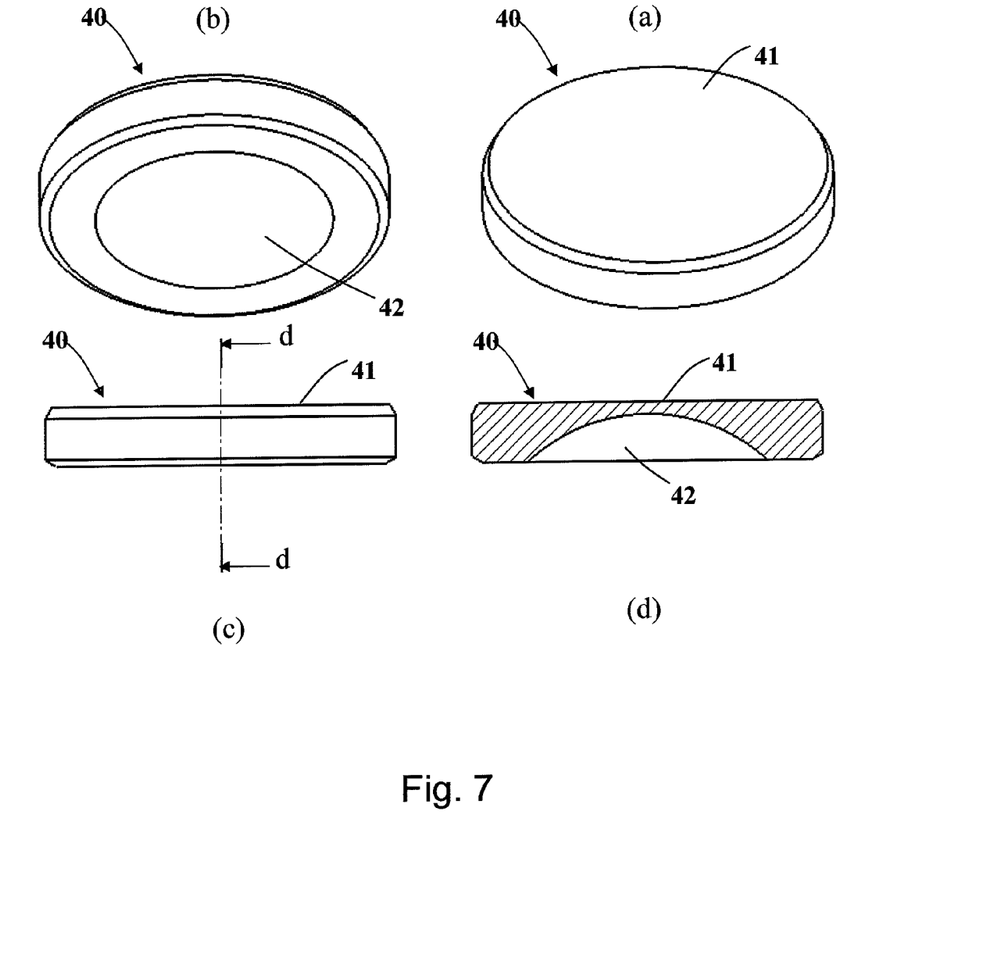
FIG. 7 shows the top perspective view (a), the bottom perspective view (b), the side view (c) and the cross sectional view (d) of the pressing plate of the present invention.

FIGS. 7, 9 and 10 disclose the pressing plate 40 which is a plate and has a locking member contact surface 41 on the top thereof and a concaved screw contact surface 42 on the underside thereof. The locking member contact surface 41 transfers a compressing force and can be a flat surface or a rough surface. The concaved screw contact surface 42 is shaped to be in contact with the head 33 of the screw 30 so that the head 42 is constantly in contact with the concaved screw contact surface 42 no matter the screw 30 is pivoted to any angle and direction. The movement of the screw 30 is not restricted in any direction.

Figure 8:
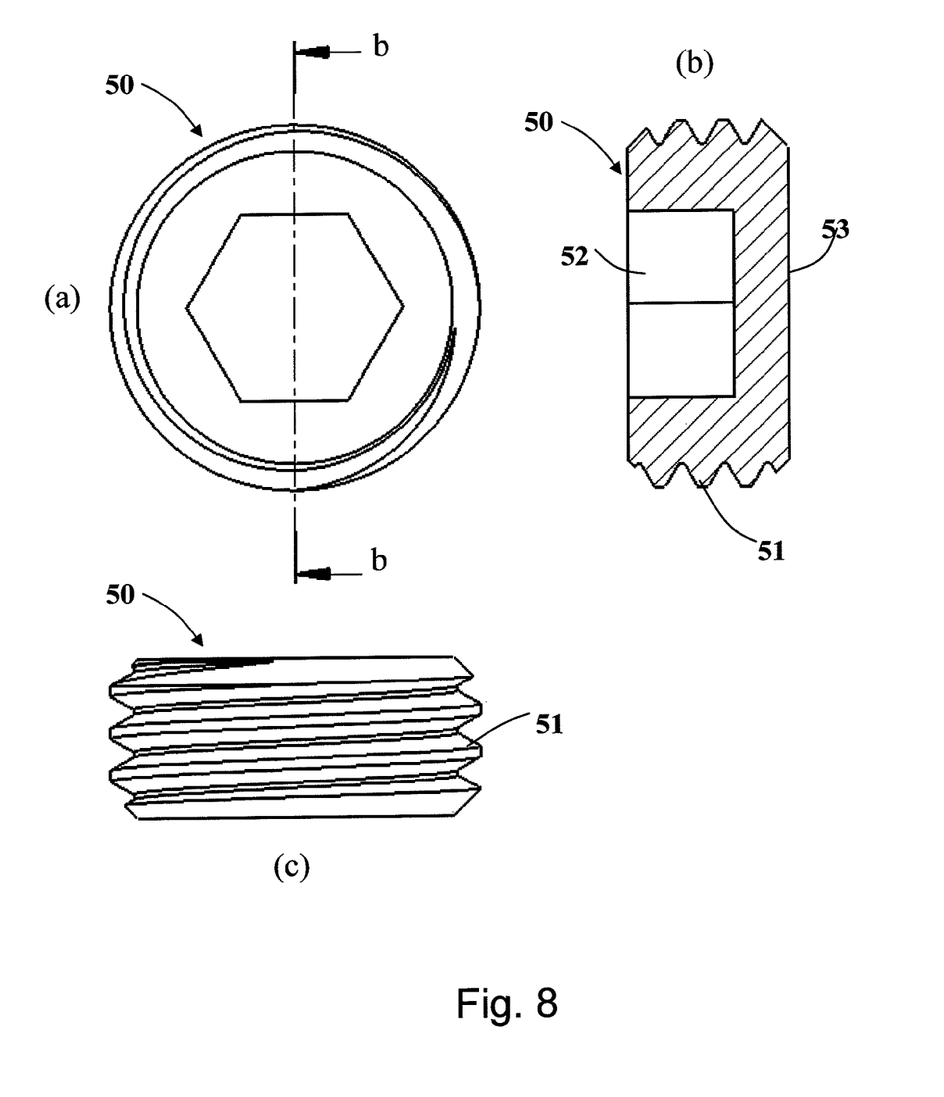
FIG. 8 shows the top perspective view (a), the cross sectional view (b) and the cross sectional view (c) of the locking member of the present invention.

FIGS. 8, 9 and 10 disclose the locking member 50 which has outer threads 51 in the outside thereof and a second recess 52 is defined in the top thereof so as to be cooperated with a tool (not shown). A washer contact surface 53 is defined in the underside of the locking member 50. The locking member 50 is connected to the connection member 20 by engaging the outer threads 51 with the inner threaded hole 131. Along with the threading action, the washer contact surface 53 provides a compression force to the pressing plate 40 so as to connect the external reconstruction plate 10, the connection member 20, the screw 30 and the pressing plate 40.

Figure 11:
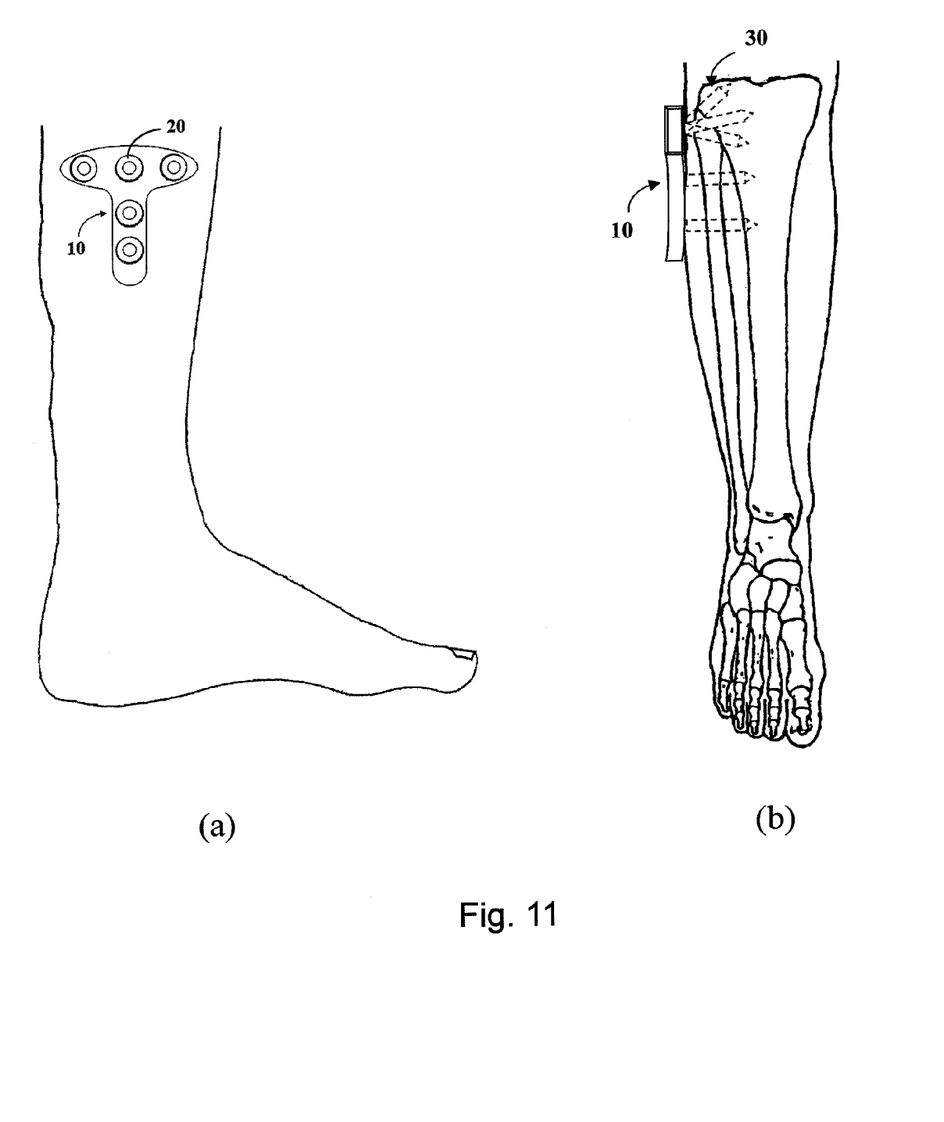
FIG. 11 is the utilization status of the preferred embodiment of the present invention for external fixing.

FIG. 11 illustrates a utilization status of the preferred embodiment of the present invention for external fixing. The external bone fixing member of the present invention uses the external reconstruction plate 10 to replace the conventional large external support frame to reduce the volume of the external fixing member. As shown in FIG. 11a, the present invention provides more operational benefits to the clinical surgeries and the debridement space is preserved. The inconvenience of activities of the patient after surgery is reduced. The screw 30 is cooperated with the external reconstruction plate 10 and can be adjusted to desired angle, as shown in FIG. 11b, so as to fix the fractured bones of different parts such as the limbs or the complicated fractures. Besides, the external reconstruction plate 10, the connection member 20, the screw 30 and the pressing plate 40 are connected to the external reconstruction plate 10 to lock the external reconstruction plate 10 to prevent the screw 30 from withdrawing, moving, angle changing or movement of the external reconstruction plate 10.

While we have shown and described the embodiment in accordance with the present invention, it should be clear to those skilled in the art that further embodiments may be made without departing from the scope of the present invention.

What is claimed is:

1. An external bone fixing member comprising:

an external reconstruction plate having multiple locking portions and each locking portion having an inner threaded hole and a through hole which shares a common axis and communicates with the inner threaded hole, a diameter of the through hole being smaller than that of the inner threaded hole;

a connection member being a ring-shaped member and having an outer threaded section and a polygonal section, the connection member having an inner threaded hole and a reception hole which communicates with the inner threaded hole of the connection member, the reception hole having a concaved and curved inner wall, the connection member connected to the external reconstruction plate by engaging the outer threaded section with the inner threaded hole of the locking portion of the external reconstruction plate;

a screw having a shank which has outer threads, a head connected to an end of the shank and having a convex and curved outer wall, a first recess defined in a top of the head, the screw extending through the connection member and the external reconstruction plate, the head of the screw being accommodated in the reception hole of the connection member, the concaved and curved inner wall being matched with the convex and curved outer wall so that the screw is pivotable;

a pressing plate having a locking member contact surface defined in a top thereof and a concaved screw contact surface defined in an underside thereof, the pressing plate located in the connection member, the concaved screw contact surface being in contact with the head of the screw, and a locking member having outer threads in an outside thereof and a second recess defined in a top thereof, a washer contact surface (53) defined in an underside of the locking member, the locking member connected to the connection member by engaging the outer threads with the inner threaded hole, the washer contact surface providing a compression force to the pressing plate to connect the external reconstruction plate, the connection member, the screw and the pressing plate.

2. The external bone fixing member as claimed in claim 1, wherein the through hole of the external reconstruction plate is a cone-shaped hole with a small opening which communicates with the inner threaded hole and shares the common axis of the inner threaded hole.

3. The external bone fixing member as claimed in claim 1, wherein a top end diameter of the reception hole of the connection member is larger than a bottom end diameter of the reception hole of the connection member, an inner wall adjacent to the top end diameter is a vertical wall.

4. The external bone fixing member as claimed in claim 1, wherein the locking member contact surface is a flat surface.

5. The external bone fixing member as claimed in claim 4, wherein the locking member contact surface is a smooth surface or a rough surface.

* * * * *